United States Patent [19]

Gamlen et al.

[11] 4,376,019

[45] Mar. 8, 1983

[54] HALOGENATION PROCESS

[75] Inventors: Philip H. Gamlen, Stockton Heath; Michael S. Henty, Lathom; David R. Sandbach, Runcorn; Brian T. Grady, Widnes, all of England

[73] Assignee: Imperial Chemical Industries PLC, London, England

[21] Appl. No.: 256,249

[22] Filed: Apr. 21, 1981

[30] Foreign Application Priority Data

May 1, 1980 [GB] United Kingdom ............... 8014404
May 1, 1980 [GB] United Kingdom ............... 8014405
May 1, 1980 [GB] United Kingdom ............... 8014406

[51] Int. Cl.³ .............................................. C25B 3/06
[52] U.S. Cl. ...................................................... 204/81
[58] Field of Search ................ 204/81, 59 R, 130, 131

[56] References Cited

U.S. PATENT DOCUMENTS

| | | | |
|---|---|---|---|
| 2,799,638 | 7/1957 | Roberts | 204/151 |
| 3,761,369 | 9/1973 | Tirrell | 204/130 |
| 4,004,993 | 1/1977 | Horner et al. | 204/130 |
| 4,076,604 | 2/1978 | Murayama et al. | 204/130 |

FOREIGN PATENT DOCUMENTS

| | | | |
|---|---|---|---|
| 17-25045 | 11/1942 | Japan | 204/81 |
| 1019437 | of 0000 | United Kingdom | 204/130 |
| 1063284 | of 0000 | United Kingdom | 204/130 |
| 1686 | 7/1980 | U.S.S.R. | 204/81 |

OTHER PUBLICATIONS

Chemisches Zentralblatt, vol. 108, No. 16, 1937, II.
Chemical Abstracts, vol. 85, No. 26, 1976; p. 479, col. 2, abstract No. 200131k.

*Primary Examiner*—R. L. Andrews
*Attorney, Agent, or Firm*—Cushman, Darby & Cushman

[57] ABSTRACT

A process for the manufacture of halogenated hydrocarbons which comprises contacting a hydrocarbon or halogenated hydrocarbon feedstock with a solution of a halide carrier to halogenate the feedstock whereby the halide carrier is reduced to a spent carrier and regenerating the halide carrier by electrolysis of the spent carrier solution from the halogenation reaction by electrolyzing the spent carrier solution in the presence of halide ions under conditions whereby deposition of metal or metal salts and liberation of elemental halogen are substantially avoided. In particular embodiments, the feedstock is halogenated using a non-aqueous solution of the halide carrier in which the ratio of halide ion:metal ion of the halide carrier is below 2:1, preferably about 1:1 and regeneration of the halide carrier is carried out in a three-compartment cell having two ion-exchange membranes or a diaphragm and a membrane. The halide carrier is a halide salt of a metal of variable valency in which the metal is in a higher valency state, especially cupric chloride or ferric chloride.

16 Claims, No Drawings

HALOGENATION PROCESS

This invention relates to a halogenation process for the manufacture of halogenated hydrocarbons from olefinic, acetylenic and aromatic hydrocarbons or partially halogenated derivatives thereof by contact with a solution of a halide carrier which is a halide salt of a metal of variable valency in which salt the metal is in a higher valency state. The halogenation reaction results in reduction of the halide carrier to a salt in which the metal is in a lower valency state; the invention includes a process for the regeneration of a halide carrier which is a salt in which the metal is in a higher valency state.

Conventional commercial processes for the manufacture of halogenated hydrocarbons from olefinic, acetylenic and aromatic hydrocarbons are essentially two-stage processes comprising the liberation, isolation and collection of elemental halogen in a first stage and reaction of the elemental halogen, often in the presence of oxygen, with the hydrocarbon in a second stage. Each of the stages, and particularly the second stage, may involve more than one operational step but the processes are essentially two-stage processes as described.

These conventional processes, due mainly to the fact that they are two-stage processes, involve high capital cost in plant and have a high energy consumption associated especially with the liberation, isolation, collection and storage of elemental halogen. In addition to high capital and operating costs, the processes have the further disadvantage of a toxicity hazard associated with the liberation, handling, storage and transport of elemental halogen.

It is known that hydrocarbons of the type described herein can be halogenated in the absence of elemental halogen by contacting them with halide carriers which are salts of metals of variable valency in which the metal is in a higher valency state, for example cupric chloride. A number of such processes have been proposed, the best known being the so-called "Kellogg" process and variants thereof wherein olefinic, acetylenic and aromatic hydrocarbons are contacted, typically in an aqueous medium at elevated temperature and pressure with a metal halide salt such as cupric chloride, and wherein the metal halide salt is regenerated in the aqueous medium using a mixture of oxygen and hydrogen chloride gas. Regeneration of the metal halide salt may be effected in situ in the halogenation reaction vessel or in a separate vessel. Processes of this type are described, for example, in United Kingdom Patent Nos 1,040,962; 1,063,175; 1,063,283; 1,063,284; 987,553; and 1,019,437.

In practice it has proved extremely difficult to operate the "Kellogg" process due to the practical difficulties in controlling the process at the high pressures required and especially in effecting regeneration of the metal halide salt in a satisfactory and controlled manner, with the result that the process has not achieved commercial acceptance and is not used on any appreciable scale in industry.

Because of its potential advantages in terms of lower capital investment, lower energy consumption, reduced operating costs and reduced safety hazards, a halogenation process for producing halogenated hydrocarbons not involving the use of elemental halogen is clearly desirable. Especially desirable is a process wherein regeneration of the halogenating agent also does not involve the use of elemental halogen, preferably not even of a hydrogen halide such as is required in the "Kellogg"—type processes.

According to the invention there is provided a process for the manufacture of halogenated hydrocarbons which comprises (a) contacting a feedstock comprising at least one hydrocarbon or halogenated hydrocarbon containing an olefinic, acetylenic or aromatic group or a halogenated hydrocarbon containing a replaceable hydrogen atom with a solution of a halide carrier which is a halide salt of a metal of variable valency in which the metal is in a higher valency state, in a liquid medium which is a solvent for the hydrocarbon or halogenated hydrocarbon feedstock so as to halogenate the feedstock whereby the halide carrier is reduced to spent carrier which is a halide salt in which the metal is in a lower valency state, and (b) regenerating the halide carrier from the spent carrier solution resulting from step (a) by electrolysing the solution in the presence of halide ions under conditions conditions whereby deposition of elemental metal or metal salts and liberation of elemental halogen during the electrolysis are substantially avoided.

For convenience and simplicity, and in the interests of clarity, the metal halide salt in which the metal is in a higher valency state is referred to herein as a "halide carrier" and the reduced form of the halide carrier in which the metal is in a lower valency state is referred to as the "reduced carrier" or "spent carrier". Thus, for instance, in the case where the metal halide salt is copper chloride, cupric chloride ($Cu^{II}$) will be called a 'halide carrier' whilst cuprous chloride ($Cu^{I}$) will be called a 'reduced carrier' or 'spent carrier'. Similarly in the case of iron chloride, ferric chloride ($Fe^{III}$) is the halide carrier whilst ferrous chloride ($Fe^{II}$) is the 'reduced carrier' or 'spent carrier'.

The halogenation stage (a) of the process is carried out using a solution of the halide carrier in a liquid medium which is a solvent for the hydrocarbon or halogenated hydrocarbon feedstock. The liquid medium or solvent may be aqueous or non-aqueous, suitable non-aqueous solvents being polar and non-polar aprotic solvents, for example dimethylformamide (DMF), dimethylsulphoxide (DMSO) halogenated hydrocarbons for example dichloromethane, carbon tetrachloride, and 1,2-dichloroethane, and especially organic nitriles, for example acetonitrile. Organic solvents are preferred which contain a nitrogen atom capable of forming a chemical bond with the metal of the reduced or spent carrier, (i.e the metal in its lower valency state) thereby imparting enhanced stability to the spent carrier species and it is for this reason that acetonitrile is the preferred organic solvent.

In the case where the halogenation reaction is carried out in an organic solvent, we have observed that the presence of water in the reaction medium has an adverse effect upon the halogenation reaction.

Accordingly when using an organic solvent such as a nitrile as the reaction medium we prefer the exclusion of water from the halogenation reaction system. However, in practice, regeneration of the halide carrier by an electrolytic technique according to the invention tends to result in water entering the organic phase and whilst the majority of water can be removed by azeotropic distillation of the mixture it is in practice difficult to ensure the complete absence of water. Thus whilst we prefer the absence of water, up to 5% by weight of water in the reaction medium can in some cases be tolerated without too great an adverse effect upon the reaction. The amount of water which can be tolerated in the reaction medium depends to some extent upon the particular halide carrier in the medium, the tolerable amount of water being greater, for example, for tolerable copper chloride than for ferric chloride.

The halogenation reaction is normally carried out at elevated temperature since whilst the reaction proceeds at room temperature the rate of reaction may be so slow as to be impracticable.

Preferably the reaction temperature is above 50° C. and, depending upon the reaction medium, may be up to 350° C. In aqueous media the reaction is usually carried out under a superatmospheric pressure of up to 1000 psi sufficient to maintain the reaction medium in liquid phase at a temperature of from 50° C. to 200° C., typically from about 120° C. to about 180° C. In general halogenation reactions in an organic solvent require lower temperatures than reactions in aqueous media and reactions in organic media may be carried out at essentially atmospheric pressure at an elevated temperature up to the boiling point of the reaction medium or under conditions of reflux; higher temperatures and superatmospheric pressure may of course be employed if desired.

The concentration of the total metal halide salts which constitute the halide carrier and reduced carrier species in the reaction medium is not critical, but owing to the high rate of usage of the halide carrier it is preferred to use the metal halides in high concentration and particularly to employ saturated or near-saturated solutions of the metal halides. In aqueous solutions concentrations of total metal halides of up to 6 M are typical. Aqueous solutions of the halide carrier/spent carrier are acidic and their pH will usually be low and in particular will typically be less than 6. If desired, the solutions may be buffered to maintain the pH at the desired level during the halogenation reaction.

During the halogenation reaction the halide carrier is reduced and the solution in fact comprises a mixture of halide carrier and reduced carrier. Indeed solutions of the halide carrier nearly always contain the reduced carrier which may constitute, for example, up to 50% by weight or more of the total metal halide salts in the solution. The relative proportions of the metal in a higher valency state, e.g. cupric ions, to metal in a lower valency state, e.g. cuprous ions, may affect the product produced in the halogenation reaction. Thus, for example, it is described in United Kingdom Pat. No 987,553 that in the halogenation of acetylene to trichloroethylene and perchloroethylene using aqueous copper chloride solution, a mole % cupric ion content of 70 to 90 in the aqueous solution favours the formation of trichloroethylene whilst a mole % cupric ion content of 85 to 100 in the solution favours the formation of perchloroethylene. Again, in United Kingdom Patent No 1,019,437 concerning the halogenation of acetylene to ethylene dichloride and vinylidene chloride, it is described that ethylene dichloride formation is favoured by a mole ratio of cupric ion to cuprous ion distinctly below unity.

The halogenation reaction conditions outlined hereinbefore are known and the halogenation reaction of the present invention may be carried out by any of the known processes and techniques. However we have devised a halogenation reaction which represents a substantial departure from the known reactions and which constitutes a new process for the manufacture of halogenated hydrocarbons. In carrying out the halogenation reaction hitherto, it has been the tendency to employ halide carrier solutions wherein the ratio of halide ion: total metal ion in the higher valency state is substantially greater than 1:1 and in particular is greater than 2:1 and typically is at least 3:1. Thus for example the ratio in typical cupric halide solutions in concentrated hydrochloric acid is generally about 3:1. We have now found, surprisingly, that halogenation reactions carried out in organic solvent media are significantly improved if the ratio of halide ion:total metal ion in the higher valency state is maintained below 2:1, preferably below 1.5:1 and in particular is about 1:1. We have observed that the maximum rate of halogenation in reactions in acetonitrile is achieved when this ratio is approximately 1:1.

According to the present invention there also is provided a process for the manufacture of halogenated hydrocarbons which comprises contacting a feedstock comprising at least one hydrocarbon or halogenated hydrocarbon containing an olefinic, acetylenic or aromatic group or a halogenated hydrocarbon containing a replaceable hydrogen atom with a solution of a halide carrier which is a halide salt of a metal of variable valency in which the metal is in a higher valency state in a non-aqueous liquid medium which is a solvent for the hydrocarbon or halogenated hydrocarbon feedstock so as to helogenate the feedstock, characterized in that the ratio of halide ions to metal ions in the higher valency state in the halide carrier solution is less than 2:1.

Preferably, the ratio is below 1.5:1 and especially preferred is a ratio of approximately 1:1.

One way of achieving the desired ratio is by incorporating in the halide carrier solution a non-halide salt of the metal of which the halide salt is the halide carrier. The added metal salt should be soluble in the halide carrier solution and examples of suitable salts for incorporating in cupric chloride solutions are copper sulphate, copper nitrate and copper tetrafluoroborate. Any non-halide salt of the metal may be employed which is soluble in the solution, though preferably the anion added with the additional salt does not form complex salts with the metal ions of the halide carrier.

Another way of achieving the desired halide: metal ratio is by adding to the solution a compound which is soluble therein and which in rthe particular reaction medium is a stronger Lewis acid than the halide carrier species such that the halide ion concentration in the solution available for complexing with the metal of the halide carrier is effectively reduced. For example aluminium trichloride may be added to a cupric chloride solution in acetonitrile to effectively reduce the chloride ion concentration available for complexing with the copper ions. Other examples include the addition of antimony pentachloride to cupric chloride solutions in dichloromethane and the addition of molybdenum pentachloride to cupric chloride solutions in carbon tetrachloride.

A further way of achieving the desired halide: metal ratio is by the use of sequestering agents.

In this embodiment of the invention wherein the halide: metal ion ratio is below 2:1, the halide carrier is preferably regenerated electrolytically as described herein but may be regenerated by any known regeneration process.

The hydrocarbon or halogenated hydrocarbon feedstock may be fed to the halogenation vessel continuously or intermittently. Efficient halogenation is dependent upon achieving intimate contact between the feedstock and the halide carrier in solution and the halogenation reaction will usually be carried out by a technique designed to improve or maximise such contact. The catalyst solution may be agitated by stirring or shaking or any desired technique, but normally the reaction will be carried out in a column, preferably a packed column, or a trickle-bed reactor. Typically, where the feedstock is gaseous, a counter-current technique is employed wherein the feedstock is passed upwardly through a column down which is flowed the halide carrier solution. In addition to enhancing contact of the feedstock and the halide carrier in the solution, the techniques described also enhance the rate of dissolution of the feedstock in the solution, as may be particularly desirable in the case where the solution is aqueous and the water-solubility of the feedstock is low. Dissolution of the feedstock is also assisted by higher pressures.

The feedstock for the halogenation reaction comprises one or more hydrocarbons or halogenated hydrocarbons containing an olefinic, acetylenic or aromatic group, or one or more halogenated hydrocarbons containing at least one replaceable hydrogen atom (i.e replaceable by a halogen atom in a substitution reaction upon contact of the feedstock with the halide carrier). The feedstock may be gaseous as in the case of the lower aliphatic olefines and acetylenic hydrocarbons and the lower halogenated hydrocarbons containing up to about 6 carbon atoms per molecule, or liquid as in the case of the higher aliphatic hydrocarbons and halogenated hydrocarbons and the aromatic hydrocarbons. Waxes or solid feedstocks may be halogenated provided they can be dissolved to a sufficient extent in the reaction medium though in the case of such feedstocks and indeed any feedstock which it is difficult to dissolve in the reaction medium it may be preferred to pre-dissolve the feedstock and feed the solution to the halogenation reaction vessel.

Mixtures of hydrocarbons and/or partially halogenated hydrocarbons may be employed as the feedstock and it will be appreciated that partially-halogenated products of the process of the invention which are capable of further halogenation may be recirculated to the reaction vessel through a product-recovery stage and, if appropriate, a halide carrier regeneration stage. Recirculation of the reaction mixture through a regeneration stage is possible since the presence in the mixture of unreacted feedstock and partially halogenated hydrocarbons does not prevent regeneration of the halide carrier. Of course, the halogenation reaction may in such cases continue outside the halogenation reaction vessel, for example in a separate regeneration vessel, and care may need to be exercised in controlling the reaction to avoid over-halogenation of the feedstock.

Because of the high demand for halogenated hydrocarbons of from 1 to about 6 carbon atoms, the feedstock will usually be a lower aliphatic olefinic or acetylenic hydrocarbon. If desired the halogenation process may incorporate a thermal cracking step. The process of the invention is especially useful, in view of the high demand for the products, for the halogenation of ethylene and acetylene. Products available by the process from the appropriate feedstock include ethylene dichloride, trichloroethylene, perchloroethylene, trichloroethane and 1,1,1-trichloroethane. If the process includes a cracking step, carbon tetrachloride, vinyl chloride and vinylidene chloride may be produced. Of particular significance is the chlorination of ethylene to ethylene dichloride (1,2-dichloroethane).

The halide carrier is a halide salt of any metal of variable valency in which salt the metal is in a higher valency state and which is soluble in and stable in the reaction medium, by which is meant has a sufficient lifetime in the reaction medium under the conditions appertaining in the system to be capable of effecting the desired halogenation reaction. Preferably the metal of the carrier is one of which the more stable halide salt is the reduced salt in which the metal is in a lower valency state such that the carrier (in which the metal is in a higher valency state) readily donates a halide ion to effect the halogenation reaction, i.e. is readily reduced to the more stable reduced carrier in which the metal is in the lower valency state. The preferred halide carriers are cupric halides in aqueous systems and ferric halides in non-aqueous systems. Mixtures of halide carriers may be used, and we have found that in aqueous media using cupric halides as carriers the reaction is improved by incorporating an additional halide carrier in the solution. The preferred additional halide carrier is ferric chloride. Examples of other halide carriers which may be used include the halides of molybdenum, thallium and antimony.

The halogenation reactions which may be effected are chlorination and bromination reactions and, in the case of at least the lower olefinic hydrocarbons, iodination reactions.

The halogenation reaction results in reduction of the halide carrier to a reduced metal halide salt in which the metal is in a lower valency state and for a practical process it is necessary to regenerate the halide carrier from the spent carrier solution. This may be effected electrolytically in the process of the present invention, by electrolysis of the spent carrier solution in the presence of halide ions. The electrolysis is carried out in an electrolytic cell under conditions such that deposition of the metal of the carrier, or its salts, during the electrolysis is substantially avoided and the liberation of elemental halogen is also substantially avoided. Avoidance of deposition of metal or metal salts involves prevention of migration of metal cations to the cathode on which metal would be deposited and avoidance of contact of the metal cations with hydroxyl ions which would result in the formation and deposition of insoluble metal hydroxides or oxides.

According to a further feature of the present invention there is provided a process for the regeneration of a halide carrier which is a salt of a metal of variable valency in which the metal is in a higher valancy state, from a solution of the spent carrier which is a halide salt in which the metal is in a lower valency state, which comprises electrolysing the spent carrier solution in the presence of halide ions under conditions whereby deposition of elemental metal or metal salts and liberation of elemental halogen during the electrolysis are substantially avoided, in a three-compartment electrolytic cell comprising an anode compartment separated by a diaphragm or an anion-exchange membrane from a central compartment and a cathode compartment separated by a cation-exchange membrane from the central compartment. Preferably the anode compartment is separated from the central compartment by an anion-exchange membrane.

Suitable conditions for the electrolysis can be created in a double-membrane electrolytic cell, that is a three-compartment cell comprising an anode compartment separated from a central compartment by an anion-exchange membrane and a cathode compartment separated from the central compartment by a cation-exchange membrane, the ion-exchange membranes defining the central compartment.

Ion exchange membranes are usually made from polymeric materials having functional groups membranes usually contain pendant groups comprising cationic groups, for example quaternary ammonium groups and tertiary amino-groups, whilst cation-exchange membranes usually contain pendant groups comprising anionic groups, for example carboxylic acid groups (—COOH—or—COONa) and sulphonyl groups (—SO$_3$H or —SO$_3$Na). Examples of suitable anion-exchange membranes are those available under the trade names 'Raipore' from RAI Corporation, 'Neosepta' from Tokuyama Soda and 'Type AR-103' from Ionics Inc. 'Rapore' membranes comprise quaternised bromides of vinyl pyridine grafted on a fluorinated base polymer. 'Neosepta' membranes are hydrocarbon polymers containing pendant amino groups. 'Type AR-103' membranes are copolymers of vinyl compounds containing quaternised ammonium groups and tertiary amino groups. Examples of suitable cation-exchange membranes include those available under the names 'Nafion' from du Pont de Nemours Co, 'Flemion' from Asahi Glass Co and 'Selemion' from Asahi Chemical Industries 'Nafion' membranes are fluoropolymers containing pendant sulphonic acid groups or derivatives of such groups. 'Flemion' membranes are fluoropolymers containing pendant carboxlic acid groups. 'Selemion' membranes are laminates of perfluorinated polymers containing sulphonic and carboxylic acid groups, as also are 'Neosepta' membranes.

In using the three-compartment cell the spent carrier solution is fed to the anode compartment to constitute the anolyte and water, or an aqueous solution, preferably distilled and de-ionised water is fed to the cathode compartment to constitute the catholyte. Electrolysis of the spent carrier solution in the anode compartment is, as stated, carried out in the presence of halide ions and these are provided in the anode compartment by migration through the anion-exchange membrane from a source of halide ions contained in the central compartment. Any source of halide ions under the conditions appertaining in the central compartment may be used, for example dilute hydrochloric acid solution, but preferably the source is an aqueous solution of an alkali metal halide, since using such a readily-available naturally-occurring source obviates the need to manufacture a synthetic source such as hydrochloric acid and in addition leads to the production of alkali metal hydroxide solutions of saleable quality in the cathode compartment, thereby improving the economics of the process.

During the electrolysis, metal cations from the halide carrier/spent carrier solution are retained in the anode compartment by the anion-exchange membrane, whilst halide ions from the central compartment migrate through the anion-exchange membrane into the anode compartment. Cations from the central compartment, e.g. alkali metal ions, migrate through the cation-exchange membrane into the cathode compartment in which electrolysis of water leads to the formation of hydrogen gas and alkali metal hydroxide. Halide ions from the central compartment are prevented by the cation-exchange membrane from entering the cathode compartment so that the alkali metal hydroxide produced in the latter compartment may be of high purity.

In the preferred regeneration process using a double-membrane cell, the feed-liquor to the central compartment is aqueous alkali metal halide solution which preferably is a saturated or near-saturated solution. In the case where the halide carrier is a metal chloride, brine is fed to the central compartment of the cell, and brine of purity similar to that conventionally used in the electrolytic generation of elemental chlorine from brine in membrane and diaphragm electrolytic cells is suitable. Of course, the greater the purity of the brine fed to the cell, the greater will be the anionic purity of the sodium hydroxide solution produced by the cell and the greater will be the lifetime of the cation-exchange membrane.

The spent carrier solution constituting the anolyte in the regeneration cell may be an aqueous solution or a solution in an organic solvent, e.g. acetonitrile, as is described hereinbefore in respect of the halogenation step of the present process; the spent carrier solution from the halogenation reaction may be fed directly (if desired after removal of desired halogenated hydrocarbon products) to the cell for halide carrier regeneration. During electrolysis of the solution, in the cell, water tends to enter the anode compartment from the central compartment, being carried through the membrane as water of hydration associated with the halide ions transported by the membrane. In the case of chloride ions, for example, as much as six water molecules may pass through the membrane with each chloride ion, although this depends upon the particular anion-exchange membrane employed; membranes are known and available which will reduce to as little as two molecules the amount of water of hydration passed with each chloride ion.

Nevertheless, in practice, water becomes entrained in the halide carrier. In the case where the solution is aqueous this effect merely results in dilution of the solution with the consequent need for re-concentration of the solution, but as is explained hereinbefore the presence of water is undesirable in halide carrier solutions in non-aqueous media such as acetonitrile. It may therefore be necessary in order to obtain optimum performance in the halogenation reaction for the regenerated halide carrier solution to be dried after the regeneration stage. Water can be removed from the solution by azeotropic distillation and if desired the resulting azeotrope may be broken (e.g. using a dichloromethane/metal-chloride system in the case of the acetonitrile-water azeotrope) and the organic solvent recovered for re-use. In practice the complete removal of water from the catalyst solution may be uneconomic so that a reduction in water-content rather than complete elimination of water will be practised. As discussed hereinbefore, the presence of a small amount of water in the halide carrier solution can be tolerated without too great an adverse effect upon the rate of the halogenation reaction, and in general the aim should be reduction of water content to an acceptable level rather than its complete elimination. In the case of essentially non-aqueous copper chloride solutions, the water content should preferably be below about 5% by weight whilst for ferric chloride solutions the water content should preferably be no more than 1% by weight.

Halide carrier regeneration may alternatively be carried out, especially in the case where the solution is aqueous, in a three-compartment cell similar to that described hereinbefore but wherein the anion-exchange membrane separating the anode and central compartments is replaced by a diaphragm. In such a cell a steady flow of liquor, e.g. alkali metal halide solution or hydrochloric acid, is ensured from the central compartment through the diaphragm into the anode compartment, thereby providing in the anode compartment the halide ions required for regeneration of the halide carrier. In such a cell, however, in order to avoid a build-up of alkali metal ions and other impurities in the halide carrier solution, we prefer to employ hydrochloric acid as the source of halide ions in the central compartment of the cell.

In the case where the spent carrier solution is an aqueous solution, the chloride ions required for regeneration of the halide carrier may be added directly to the spent carrier solution in the anode compartment of the cell. In this case a single-membrane cell may be employed in which the membrane is an anion-exchange membrane. In a single-membrane cell the catholyte may be, for example, water. Where addition of chloride ions is directly to spent carrier solution it is preferred to employ aqueous hydrochloric acid solution as the source of the ions since the addition of cations such as alkali metal ions to the solution is undesirable. Alternatively when using a single-membrane cell (anion-exchange membrane) the chloride ions may be provided in the cathode compartment and allowed to migrate through the membrane into the anode compartment. Again in this case, hydrochloric acid is preferred to alkali metal chloride solutions as the source of chloride ion and the catholyte may be, for example, an aqueous hydrochloric acid solution. The latter embodiment is appropriate, for example, in cases where the halide carrier/spent carrier solution is a non-aqueous medium such as acetonitrile to which direct addition of aqueous hydrochloric acid is obviously undesirable.

As stated, electrolytic regeneration of the halide carrier is under conditions such that liberation of elemental halogen is substantially avoided. This can be achieved by ensuring that electrolysis is carried out at an electrode potential, especially an anode potential, below the threshold potential required for formation of elemental halogen. The optimum anode potential will depend upon the particular anode employed and especially upon the working surface of the anode, but as a guide the anode potential for regenerating metal chloride salts will usually be maintained below 1.5 volts compared to the standard hydrogen electrode, and in practice we prefer in most cases to employ an anode potential of from 0.3 to 1.4 volts. The cathode potential may be, for example, from 0.5 to 1.6 volts.

The anodes and cathodes of the electrolytic cell may be any of those known in the art for electrolysis of alkali metal halide solutions and which are resistant to attack by strong, for example saturated, metal halide solutions. Thus the electrodes may be of any desired shape and may be made of any of the materials known for electrodes. The anode may be made, for example, of graphite, platinum, lead oxide or a film-forming metal, e.g. titanium coated with an electro-conducting, electrocatalytically active coating, e.g. platinum metals or their oxides, for example ruthenium oxide, or a mixture of a platinum metal oxide and a film-forming metal oxide. The cathode may be made, for example, of steel, lead oxide, copper, 'Monel' metal or graphite. The anode and the cathode may be of the same or a different material.

The halide carrier and spent carrier solutions are strongly acidic and highly corrosive liquors so that any equipment with which they come into contact must be resistant to corrosion by strong acids or protected against corrosion. Typically reaction vessels, cells and other items of equipment with which the solution comes into contact will be made of or provided with a protective coating of an acid-resistant polymer, for example a fluorine-containing polymer or copolymer, notably polytetrafluoroethylene and polypropylene.

The electrolysis may be carried out at room temperature and pressure, though in general the temperature of the spent carrier solution in the anode compartment of the cell will be above room temperature and in particular will be in the range of 50° C. to 90° C. in the case of aqueous solutions and up to the boiling point of the solution in the case of essentially non-aqueous solutions.

Regeneration of the halide carrier can be carried out in a cell separated from the halogenation reaction vessel, for example by circulating the carrier/spent carrier solution between the halogenation vessel and the anode compartment of the regeneration cell, or it may be carried out in the halogenation vessel. In the latter case the halogenation vessel is also the anode compartment of the regeneration cell, or put another way the halogenation reaction is carried out in the anode compartment of the regeneration cell, there being provided in the cell inlet means for introducing the hydrocarbon or halogenated hydrocarbon feedstock into the anode compartment.

The temperature of the carrier/spent carrier solution during the electrolysis will depend upon whether regeneration is carried out in the halogenation vessel or in a separate cell, since in the former case the temperature will necessarily be that at which the halogenation reaction is effected. As described hereinbefore, the halogenation temperature may be appreciably greater than 90° C. and may be up to 300° C. to 350° C., and the temperature range of 50° C. to 90° C. quoted hereinbefore applies to the case where regeneration is carried out in a cell separated from the halogenation vessel. Since the optimum conditions for the halogenation reaction, particularly temperature and pressure, may differ appreciably from the optimum conditions for halide carrier regeneration, it is usually more convenient to carry out regeneration in a separate vessel. As well as enabling the creation of optimum conditions for the separate reactions, operation in separate vessels has the additional advantages of simplifying asscociated operations such as isolation and collection of desired halogenated hydrocarbon products, matching the rate of halide carrier reduction during halogenation with the rate of halide carrier regeneration, and purifying and drying (where the solution is essentially non-aqueous) the halide carrier solution.

It is to be understood that whilst for convenience the cell compartment between and defined by the membranes (or the membrane and diaphragm in cells wherein a diaphragm is used instead of an anion-exchange membrane) is referred to herein as the central compartment it is not intended to be implied that the compartment needs to be located in a central position with respect to the geometry of the cell; it is meant only that between the anode and cathode or between each anode and cathode in multi-electrode cells there are located two membranes (or a membrane and a diaphragm) with a gap between them which is not in direct communication with the anode or cathode compartments. Nor is it intended to imply that the anode, cathode and central compartments are of the same or even approximately the same size. The cell may be of any type, for example a tank-type cell, though we prefer to employ a filter-press cell.

The invention is illustrated but in no way limited by the following examples, in which the general procedures referred to are as follows:

I Halogenation Reaction

A Liquid feedstocks

A solution (100 ml) of a halide carrier (i.e. a metal halide salt in which the metal is in a higher valency state) or of a mixture of salts of metals including a halide carrier in an appropriate solvent was placed in a glass reactor fitted with a paddle or magnetic stirrer, a condenser, an inlet port for gas and a sample-withdrawal port. The solution was heated to the desired temperature and purged with nitrogen gas via the gas inlet port at a rate of 50 ml/min until equilibrium conditions were achieved, such conditions being denoted by total removal of oxygen from the system and complete dissolution of metal salts. The liquid feedstock (for example cyclohexene) was then added through the sample port in an amount equal to or in excess of the calculated stoichiometric amount for the expected halogenation reaction.

The resulting halogenation reaction was allowed to proceed for a period of up to 5 hours during which time samples of the solution were removed at intervals and analysed for halogenation products. Organic components, e.g. unreacted feedstock and halogenated derivatives thereof, were determined by gas-liquid chromatography techniques whilst the concentrations of the halide carrier and the reduced halide carrier were determined by titrimetric and/or polarographic techniques.

B Gaseous feedstocks

The procedure was essentially the same as for liquid feedstocks except that before the halide carrier solution was heated to the desired temperature, the system was purged at room temperature with nitrogen gas at a rate of 50 ml/min and then with the gaseous feedstock at a rate of 50 ml/min until equilibrium conditions had been achieved. The halogenation reaction was allowed to proceed for a period of up to 5 hours during which time samples of the solution were removed at intervals and analysed as described under procedure A.

II Regeneration Procedure

A three-compartment filter-press type electrochemical cell was assembled comprising an anode compartment separated by an anion-exchange membrane from a central compartment and a cathode compartment separated by a cation-exchange membrane from the central compartment. The anode and cathode compartments were of equal size of approximately 15 cm×15 cm×1 cm and the central compartment was of size 15 cm×15 cm×0.25 cm. Each compartment was provided with an inlet port and an outlet port for cell liquor so that if desired liquor could be fed continuously to each compartment. Except as indicated in one experiment (60° C.) the cell was used at ambient temperature (approx 25° C.) and in each case electrolysis was carried out for a period of several hours, typically 4 to 5 hours. In each electrolysis the anolyte was comprised by a solution of a reduced halide carrier (cuprous chloride) or a mixture of halide carrier and reduced carrier in an appropriate solvent.

EXAMPLE 1

Using general procedure IA described above, cyclohexene was chlorinated to 1,2-dichlorocyclohexane using cupric chloride halide carrier in solution in acetonitrile, in a series of experiments for which the reaction conditions and results are shown in Table 1. The halide carrier is regenerable from the resulting spent carrier solution by general procedure II described above.

TABLE 1

| Expt. No | Carrier Conc. (M) | Olefin Conc. (M) | Temp (°C.) | Time (mins) | Yield* (%) |
|---|---|---|---|---|---|
| 1 | 0.17 | 1.36 | 81 | 10 | 23.7 |
|  |  |  |  | 100 | 52.3 |
|  |  |  |  | 300 | 63.6 |
| 2 | 0.20 | 0.20 | 81 | 10 | 20.0 |
|  |  |  |  | 90 | 49.3 |
|  |  |  |  | 272 | 54.9 |
| 3 | 0.04 | 0.16 | 81 | 60 | 47.6 |
| 4 | 0.04 | 0.16 | 81 | 60 | 39.0 |
| (+ CuCl 0.005) |  |  |  |  |  |
| 5 | 0.04 | 0.16 | 81 | 60 | 32.6 |
| (+ CuCl 0.01) |  |  |  |  |  |
| 6 | 0.04 | 0.16 | 81 | 60 | 26.8 |
| (+ CuCl 0.02) |  |  |  |  |  |
| 7 | 0.08 | 0.32 | 81 | 60 | 47.5 |
| 8 | saturated | 1.0 | reflux | 60 | — |

*% Yield based on initial concentration of cupric chloride.

EXAMPLE 2

This example illustrates the adverse effect upon halogenation reactions of water in essentially non-aqueous halide carrier solutions.

Using general procedure IA, cyclohexene was chlorinated at 81° C. using a solution of cupric chloride or ferric chloride in acetonitrile in a series of experiments in which water was added to the solution. Reaction conditions and results are shown in Table 2. The halide carrier is regenerable from the resulting spent carrier solution by general procedure II.

TABLE 2

| No | Water (%) | Halide Carrier | Conc. (M) | Olefine Conc (M) | Time (min) | Yield* (%) |
|---|---|---|---|---|---|---|
| 1 | 0 | ↑ |  |  |  | 47.5 |
| 2 | 5 | ↑ |  |  |  | 16.4 |
| 3 | 10 | ↑ |  |  |  | 4.8 |
| 4 |  | CuCl$_2$ | 0.08 | 0.32 | 60 | 1.8 |
| 5 | 20 | ↓ |  |  |  |  |
|  | 25 | ↓ |  |  |  | 1.6 |
| 6 | 0 | ↑ | 0.1 | 0.4 | 60 | 33.8 |
| 7 | 0.02 | ↑ | 0.2 | 1.9 | .2 | 30.2 |
|  |  | ↑ |  |  | 10 | 32.1 |
|  |  | ↑ |  |  | 60 | 33.0 |
| 8 | 0.6 | ↑ | 0.16 | 1.9 | 10 | 19.4 |
|  |  | FeCl$_3$ |  |  |  |  |
|  |  | ↓ |  |  | 90 | 25.1 |
|  |  | ↓ |  |  | 200 | 26.7 |
| 9 | 0.8 | ↓ | 0.19 | 0.16 | 60 | 25.8 |
| 10 | 1.8 | ↓ | 0.19 | 0.16 | 60 | 9.4 |
| 11 | 5.8 | ↓ | 0.18 | 0.16 | 60 | 2.7 |

*Based on metal halide.

EXAMPLE 3

Using general procedure IA cyclohexene was chlorinated to 1,2-dichlorocyclohexane using an aqueous solution of cupric chloride or ferric chloride as shown in Table 3.

TABLE 3

| Carrier | Conc | Olefin Conc | Temp | Time (mins) |
| --- | --- | --- | --- | --- |
| CuCl$_2$ | saturated | saturated | reflux | 60 |
| FeCl$_3$ | 3.0 | saturated | reflux | 60 |

The halide carrier can be regenerated from the resulting spent carrier solution by general procedure II.

EXAMPLE 4

This example illustrates the effect on the chlorination of cyclohexene using a solution of cupric chloride in acetonitrile of reducing the Cl$^-$/Cu$^{++}$ ratio in the solution.

Cyclohexene was chlorinated by general procedure IA under the conditions shown in Table 4. Experiments 1 to 8, 10 to 16 and 19 to 23 demonstrate the addition to the halide carrier (cupric chloride) solution of copper salts to effectively increase the copper ion content of the carrier solution and decrease the chloride: cupric ion ratio, whilst Experiments 17 and 18 illustrate the addition to the carrier solution of metal halides which are stronger Lewis acids than cupric chloride, again to decrease the chloride: cupric ion ratio. Experiment 9 is included for purposes of comparison and illustrates the use of cupric chloride solution wherein the Cl$^{-1}$/Cu$^{++}$ ratio is relatively high (2.5/1).

TABLE 4

| Expt No | CuCl$_2$ Conc (M) | Additive | Conc (M) | Cl/Ca ratio | Olefinic Conc (M) | Temp (°C.) | Time (mins) | Yield* (%) |
| --- | --- | --- | --- | --- | --- | --- | --- | --- |
| 1 | | | | 2.0 | | | | 52.9 |
| 2 | | | | 1.993 | | | | 49.6 |
| 3 | | | | 1.992 | | | | 49.9 |
| 4 | 0.1 | CuSO$_4$ | | 1.990 | | 81 | 60 | 50.2 |
| | | | | | 0.4 | | | |
| 5 | | | | 1.988 | | | | 50.7 |
| 6 | | | | 1.984 | | | | 51.1 |
| 7 | | | | 1.979 | | | | 55.8 |
| 8 | | | | 1.855 | | | | 60.3 |
| 9 | 0.1 | NONE | — | 2.5 | 0.47 | 81 | 60 | 42.3 |
| 10 | 0.05 | Cu(BF$_4$)$_2$ | 0.05 | 1.0 | 0.47 | 81 | 60 | 81.8 |
| 11 | 0.02 | Cu(BF$_4$)$_2$ | 0.08 | 0.4 | 0.47 | 81 | 60 | 41.0 |
| 12 | ↑ | ↑ | | | | | 2 | 29.6 |
| 13 | | ↑ | | | | | 11 | 58.4 |
| 14 | 0.05 | Ca(BF$_4$)$_2$ | 0.05 | 1.0 | 0.4 | 81 | 31 | 69.6 |
| 15 | ↓ | ↓ | | | | | 60 | 68.8 |
| 16 | | ↓ | | | | | 100 | 72.8 |
| 17 | 0.05 | FeCl$_3$ | 0.05 | ↑ | — 0.4 | 81 | 60 | 50.0 |
| 18 | 0.05 | AlCl$_3$ | 0.05 | ↑ | 0.4 | 81 | 60 | 66.3 |
| 19 | ↑ | ↑ | | ↑ | | | 60 | 49.6 |
| 20 | ↑ | ↑ | | ↑ | | | 65 | 53.9 |
| 21 | 0.045 | Cu(BF$_4$)$_2$ | 0.045 | 1.0 | 0.35 | 70 | 60 | 60.0 |
| 22 | ↓ | ↓ | | ↓ | | 75 | | 63.5 |
| 23 | ↓ | ↓ | | ↓ | | 81 | | 66.1 |

*Based on metal halide carrier consumed.

EXAMPLE 5

Ethylene was halogenated to yield 1-chloro-2-iodo ethylene using general procedure IB. The halide carrier solution was a saturated solution of cupric chloride in acetonitrile containing 0.1 M elemental iodine, and the olefin concentration in the solution was saturation. Reaction was carried out at 20° C. and after 60 minutes the yield of 1-chloro-2-iodo ethylene was greater than 50% based on the initial, concentration of total chloride and iodine.

The cupric chloride is regenerated from the spent carrier solution by general procedure II.

EXAMPLE 6

Ethylene was chlorinated to 1,2-dichloroethane using general procedure IB and the halide carriers and reaction conditions shown in Table 5. In each experiment the olefin concentration was saturation and the reaction temperature was 20° C.

The halide carrier is regenerated by general procedure II.

TABLE 5

| Expt No | Solvent | Halide Carrier-Conc (M) | Yield* (%) |
| --- | --- | --- | --- |
| 1 | CH$_2$Cl$_2$ | SbCl$_5$-0.23 | 100 |
| 2 | CH$_2$Cl$_2$ | MoCl$_5$-satd | 23.5 |
| 3 | CCl$_4$ | SbCl$_5$-0.23 | 65.2 |
| 4 | CCl$_4$ | MoCl$_5$-satd | 36.0 |

*Yield after 10 mins based on metal halide.

EXAMPLE 7

Cyclohexene was chlorinated by general procedure IA under the reaction conditions shown in Table 6.

The antimony pentachloride is regenerated by general procedure II.

TABLE 6

| Solvent | Halide | Conc (M) | Olefine (M) | Temp (°C.) | Yield (%) |
| --- | --- | --- | --- | --- | --- |
| CCl$_4$ | SbCl$_5$ | 0.23 | 0.99 | 20 | 71.0 |
| CH$_2$Cl$_2$ | SbCl$_5$ | 0.23 | 0.99 | 20 | 57.5 |

*Based on metal chloride.

EXAMPLE 8

This example illustrates the electrolytic regeneration of cupric chloride from aqueous and non-aqueous solutions of cuprous chloride by a batch technique, using general procedure II described hereinbefore.

The following electrolytic cell was assembled.

| Anode | Membrane | — | Membrane | Cathode |
|-------|----------|---|----------|---------|
| Pt | Permutit | — | 'Nafion' 390 | Pt |

In three experiments the cell was used to produce cupric chloride solutions from the following anolyte feed solutions of cuprous chloride.

Experiment 1
 Anolyte:
  $CuCl_2$ (3.6 M)
  CuCl (0.9 M)
  HCl (3.0 M)
  (Aqueous - 200 ml)
Experiment 2
 Anolyte:
  $CuCl_2$ (3.6 M)
  CuCl (0.9 M)
  (Aqueous - 200 ml)
Experiment 3
 Anolyte:
  CuCl (0.1 M)
  (in $CH_3N$ - 200 ml)

In each experiment the solution in the central compartment of the cell was 31 ml of aqueous sodium chloride solution (25%) and the catholyte was 200 ml of aqueous sodium chloride solution (1 M).

The resulting solutions of cupric chloride are used for halogenating feedstocks by general procedures IA and IB.

The following results were obtained.

| | Current Efficiency* | | | | Cell | Current |
|---|---|---|---|---|---|---|
| | Anodic Processes | | Cathodic Processes | | Voltage | Density |
| Experiment 1 | $Cu^+$ 102% | $Cu^{++}$ | $H_2O$ 95% | $\frac{1}{2}H_2 + OH^-$ | 12.2V | 160 $Am^{-2}$ |
| Experiment 2 | $Cu^+$ 103% | $Cu^{++}$ | $H_2O$ 58% | $\frac{1}{2}H_2 + OH^-$ | 10.8V | 1428 $Am^{-2}$ |
| Experiment 3 | $Cu^+$ 112% | $Cu^{++}$ | $H_2O$ 118% | $\frac{1}{2}H_2 + OH^-$ | 28V | 285 $Am^{-2}$ |

*Results quoted are as determined experimentally, although maximum efficiency is in fact 100%.

EXAMPLE 9

Using the electrolytic cell described in Example 8 except that the cathode was MONEL metal instead of platinum, the following aqueous anolyte was fed continuously to the anode compartment at the rate of 20 ml/second.
 Anolyte
  $CuCl_2$ (3.6)
  CuCl (0.9 M)
  HCl (1.0 M)

Sodium chloride solution (25%) was fed continuously to the central compartment at the rate of 5 ml/second and de-ionised water was fed continuously to the cathode compartment at the rate of 5 ml/second.

Current efficiency (as determined within experimental accuracy) for the anodic process $Cu^+ Cu^{++}$ was 97.3% whilst that for the cathodic process $H_2O$ $\frac{1}{2}H_2 + OH^{-1}$ was 111.5%. Cell voltage was 3.5 V and current density was 1700 $Am^{-2}$.

The resulting cupric chloride solution is used to halogenate feedstocks by general procedure IA and IB.

EXAMPLE 10

This example illustrates the simultaneous regeneration of halide carrier and chlorination of cyclohexene in the anode compartment of an electrolyte cell.

Using the cell described in Example 8 and a batch technique, the following anolyte was placed in the anode compartment.
 Anolyte
  $CuCl_2$ (0.09 M)
  CuCl (0.01 M)
  Cyclohexene (0.4 M)
  Acetonitrile (200 ml)

The liquid in the central compartment was 25% aqueous sodium chloride solution (31 ml) and the catholyte was IM aqueous sodium chloride solution (200 ml). The cell liquors were heated to 60° C. prior to passage of electric current through the cell and this temperature was maintained throughout the resulting simultaneous halogenation reaction and regeneration reaction.

Cell voltage was 14.3 V and current density was 142.5 A $m^{-2}$. After passage of a charge of 7000 coulombs, the anolyte was analysed and was found to contain 1,2-dichlorocyclohexane (0.34 M) and cupric chloride with little trace of cuprous chloride.

EXAMPLE 11

An aqueous carrier solution of copper chloride (2.14 M cupric chloride, 0.57 M cuprous chloride) in conc. hydrochloric acid was prepared and divided into three equal fractions.

The first fraction of the carrier solution was used to chlorinate ethylene to 1,2-dichloroethane by general procedure IB under the reaction conditions given in the Table below. The Space-Time-Yield (STY) of 1,2-dichloroethane for the reaction was 0.35 moles/litre/hour.

The second and third fractions of the carrier solution were electrolysed by general procedure II to yield the following aqueous solutions:-
(a) 2.54 M cupric chloride: 0.26 M cuprous chloride
(b) 2.39 M cupric chloride: 0.42 M cuprous chloride Solutions (a) and (b) were separately used to chlorinate ethylene to 1,2-dichloroethane by general procedure IB with resulting STY of 0.62 and 0.63 moles/litre/hour respectively.

| Halide Carrier (M) | Total Pressure (psi) | Ethylene Pressure (psi) | Time hrs | Temp (°C.) | STY M/l/h |
|---|---|---|---|---|---|
| 2.14 $CuCl_2$:0.57 CuCl | 110 | 95 | 6 | 130 | 0.35 |
| 2.54 $CuCl_2$:0.26 CuCl | 110 | 95 | 5 | 130 | 0.62 |
| 2.39 CuCl:0.42 CuCl | 110 | 95 | 5 | 130 | 0.63 |

EXAMPLE 12

This example illustrates the increased STY obtained by adding additional metal chlorides to aqueous cupric chloride solutions used in the chlorination of ethylene to 1,2-dichloroethane using general procedure IB. The carrier solutions and yields are shown in the Table. All reactions were carried out at 130° C. for 4 hours under a total pressure of 110 p.s.i. and ethylene pressure of 95 p.s.i. Experiment 5 was carried out on a solution not containing copper chloride and is included for purposes of comparison.

| Experiment No | Carrier Solution | | | | | STY (M/l/h) |
|---|---|---|---|---|---|---|
| | $CuCl_2$ (M) | CuCl (M) | $FeCl_3$ (M) | $ACCl_3$ (M) | $CaCl_2$ (M) | |
| 1 | 2.80 | — | — | — | — | 0.28 |
| 2 | 2.80 | — | — | 2.80 | — | 4.14 |
| 3 | 2.80 | — | 2.80 | — | — | 7.68 |
| 4 | 2.80 | — | — | — | 5.5 | 2.84 |
| 5 | — | — | 2.80 | — | 2.80 | 0.71 |

EXAMPLE 13

This example illustrates the improvement in rate of chlorination obtained using non-aqueous (acetonitrile) solutions of cupric chloride by reducing the chloride ion: cupric ion ratio to 1:1 by incorporating copper tetrafluoroborate in the carrier solution.

Ethylene was chlorinated to 1,2-dichloroethane by general procedure IB under a total pressure of 200 p.s.i. and ethylene pressure of 195 p.s.i. at 100° C. for a period of 5 hours.

| Carrier Solution | | $Cu^{++}/Cl^-$ ratio | STY (M/l/h) |
|---|---|---|---|
| $CuCl_2$ (M) | $Cu(BF_4)_2$ (M) | | |
| 0.2 | — | 1:3 | 1.61 |
| 0.1 | 0.2 | 1:1 | 2.50 |

EXAMPLE 14

Ethylene was chlorinated to 1,2-dichloroethane using aqueous cupric chloride solution by general procedure IB under a total pressure of 110 p.s.i. ad ethylene pressure of 95 p.s.i. at 130° C. for a period of 4 hours.

| Carrier Solution | | $Cu^{++}/Cl^-$ ratio | STY (M/l/h) |
|---|---|---|---|
| $CuCl_2$ (M) | $Cu(BF_4)_2$ (M) | | |
| 2.8 | — | 1:3 | 0.28 |
| 2.8 | 2.8 | 1:1 | 0.38 |
| 5.6 | — | 1:3 | 7.64 |

These results demonstrate that in aqueous cupric chloride solutions, reducing the cupric ion/chloride ion ratio to 1:1 has no significant effect upon the rate of chlorination.

We claim:

1. A process for the manufacture of halogenated hydrocarbons which comprises
    (a) contacting a feedstock comprising at least one hydrocarbon or halogenated hydrocarbon containing an olefinic, acetylenic or aromatic group or a halogenated hydrocarbon containing a replaceable hydrogen atom, with a solution of a halide carrier which is a halide salt of a metal of variable valency in which the metal is in a higher valency state in a liquid medium which is a solvent for the hydrocarbon or halogenated hydrocarbon feedstock so as to halogenate the feedstock whereby the halide carrier is reduced to a spent carrier which is a halide salt of the metal in which the metal is in a lower valency state, and
    (b) regenerating the halide carrier from the spent carrier solution resulting from step (a), characterised in that regeneration of the halide carrier from the spent carrier solution is by electrolysing the spent carrier solution in the presence of halide ions under conditions whereby deposition of elemental metal or metal salts and liberation of elemental halogen during the electrolysis are substantially avoided.

2. A process as claimed in claim 1 characterised in that the metal halide carrier is a metal chloride which is regenerated by electrolysis in the presence of chloride ions, characterised in that the chloride ions present during electrolysis of the spent carrier solution are generated in situ by electrolysis of aqueous sodium chloride solution.

3. A process as claimed in claim 1 or 2 characterised in that the solution of the halide carrier is an aqueous solution.

4. A process as claimed in claim 1 or 2 characterised in that the solution of the halide carrier is a solution in acetonitrile.

5. A process as claimed in claim 1 chacterised in that the spent carrier is a more stable species than the halide carrier.

6. A process as claimed in claim 3 characterised in that the halide carrier solution is aqueous cupric chloride solution.

7. A process as claimed in claim 4 characterised in that the halide carrier solution is a solution of ferric chloride in acetonitrile.

8. A process as claimed in claim 6 characterised in that the halide carrier solution comprises an additional halide salt of a metal of variable valency other than copper in which the metal is in a higher valency state.

9. A process as claimed in claim 8 characterised in that the additional halide salt is ferric chloride.

10. A process as claimed in claim 1 characterised in that step (b) is carried out in a three-compartment electrolytic cell comprising an anode compartment separated from a central compartment by an anion-exchange membrane, and a cathode compartment separated from the central compartment by a cation-exchange membrane, the ion-exchange membranes defining the central compartment.

11. A process as claimed in claim 1 characterised in that the halide carrier solution is aqueous and step (b) is carried out in a three-compartment electrolytic cell comprising an anode compartment separated from a central compartment by a diaphragm, and a cathode compartment separated from the central compartment by a cation-exchange membrane, the diaphragm and the cation-exchange membrane defining the central compartment.

12. A process as claimed in claim 10 or 11 characterised in that the spent carrier solution is fed to the anode compartment, the source of halide ions is fed to the central compartment and water is fed to the cathode compartment.

13. A process as claimed in claim 1 characterised in that the halide carrier is in solution in acetonitrile and the ratio of halide ion: total metal ion in the solution is less than 2:1.

14. A process as claimed in claim 1 characterised in that regeneration of the halide carrier in step (b) is carried out in an electrolytic cell wherein the anode potential is from 0.3 volt to 1.4 volt.

15. A process as claimed in claim 14 characterised in that the cathode potential is from 0.5 volt to 1.6 volt.

16. A process as claimed in claim 1 characterised in that the feedstock is ethylene or acetylene.

* * * * *